United States Patent
Chodkowski et al.

(10) Patent No.: US 10,195,379 B2
(45) Date of Patent: Feb. 5, 2019

(54) PATIENT INTERFACE HAVING ILLUMINATED PORTION

(71) Applicant: KONINKLIJKE PHILIPS N.V., Eindhoven (NL)

(72) Inventors: Lauren Patricia Chodkowski, Pittsburgh, PA (US); Susan Marie Mals, Monroeville, PA (US); Matthew Answine, Apollo (NL); Jonathan Sayer Grashow, Pittsburgh, PA (US); Robert William Baiko, Pittsburgh, PA (US); Richard Thomas Haibach, Verona, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 631 days.

(21) Appl. No.: 14/381,708

(22) PCT Filed: Mar. 1, 2013

(86) PCT No.: PCT/IB2013/051642
§ 371 (c)(1),
(2) Date: Aug. 28, 2014

(87) PCT Pub. No.: WO2013/132397
PCT Pub. Date: Sep. 12, 2013

(65) Prior Publication Data
US 2015/0040896 A1    Feb. 12, 2015

Related U.S. Application Data

(60) Provisional application No. 61/607,145, filed on Mar. 6, 2012.

(51) Int. Cl.
| | |
|---|---|
| *A61M 16/00* | (2006.01) |
| *A61M 16/06* | (2006.01) |
| *A61M 16/08* | (2006.01) |
| *A61M 39/10* | (2006.01) |
| *A61M 21/00* | (2006.01) |

(52) U.S. Cl.
CPC .... *A61M 16/0051* (2013.01); *A61M 16/0003* (2014.02); *A61M 16/021* (2017.08);
(Continued)

(58) Field of Classification Search
CPC .......... A61M 16/0051; A61M 16/0003; A61M 16/0633; A61M 16/0622; A61M 16/06;
(Continued)

(56) References Cited

U.S. PATENT DOCUMENTS 3,595,228 A * 7/1971 Simon ............... A61M 16/0051
128/202.22
4,155,357 A * 5/1979 Dahl ................. A61M 16/0051
128/202.22
(Continued)

FOREIGN PATENT DOCUMENTS

| CN | 201418956 Y | 3/2010 |
|---|---|---|
| DE | 102007015037 B3 | 6/2008 |

(Continued)

*Primary Examiner* — Gregory Anderson
*Assistant Examiner* — Victoria Murphy
(74) *Attorney, Agent, or Firm* — Michael W. Haas

(57) ABSTRACT

A coupling for use in a system (2) for communicating a flow of gas from a pressure generating device (4) to an airway of a patient includes a first portion (16, 16', 16") adapted to be coupled in fluid communication with the pressure generating device and a second portion (10) selectively coupled to the first portion. The second portion is adapted to be coupled in fluid communication with the airway of the patient. At least one of the first portion and the second portion includes an illuminated portion (18, 20), the illuminated portion being adapted to be visible to a patient when the first and second portions are uncoupled and adapted to be not visible to a user when the first and second portions are coupled. The illuminated portion assists a user in locating and recoupling the first and second portions of the coupling in a darkened room.

6 Claims, 13 Drawing Sheets

(52) U.S. Cl.
CPC ........ *A61M 16/06* (2013.01); *A61M 16/0622* (2014.02); *A61M 16/0633* (2014.02); *A61M 16/0683* (2013.01); *A61M 16/0816* (2013.01); *A61M 16/0875* (2013.01); *A61M 39/10* (2013.01); *A61M 2016/0033* (2013.01); *A61M 2021/0044* (2013.01); *A61M 2021/0083* (2013.01); *A61M 2039/1044* (2013.01); *A61M 2205/14* (2013.01); *A61M 2205/15* (2013.01); *A61M 2205/18* (2013.01); *A61M 2205/3334* (2013.01); *A61M 2205/3386* (2013.01); *A61M 2205/583* (2013.01); *A61M 2205/587* (2013.01)

(58) Field of Classification Search
CPC .......... A61M 16/0816; A61M 16/0875; A61M 16/0683; A61M 2016/0033; A61M 2205/3386; A61M 2205/15; A61M 2205/3334; A61M 2205/18
See application file for complete search history.

(56) References Cited

U.S. PATENT DOCUMENTS

| | | | |
|---|---|---|---|
| 5,913,883 A | 6/1999 | Alexander | |
| 6,454,789 B1* | 9/2002 | Chen | A61N 5/062 362/572 |
| 7,311,261 B1* | 12/2007 | Kennedy | G02B 27/20 235/462.22 |
| 2003/0183294 A1* | 10/2003 | Carlson | A61M 16/08 138/129 |
| 2004/0194195 A1 | 10/2004 | Palmer | |
| 2001/0103926 | 5/2007 | Brooks | |
| 2007/0103962 A1 | 5/2007 | Brooks | |
| 2011/0232645 A1* | 9/2011 | Smith | A61M 16/06 128/205.23 |
| 2011/0265792 A1 | 11/2011 | Crawford | |
| 2014/0031755 A1* | 1/2014 | Williams | A61M 39/10 604/175 |

FOREIGN PATENT DOCUMENTS

| | | | | |
|---|---|---|---|---|
| DE | 102012004249 A1 * | 9/2013 | | A61M 39/10 |
| EP | 1074275 A1 | 2/2001 | | |
| EP | 2371411 A1 | 10/2011 | | |
| JP | 2011107111 A | 2/2011 | | |
| WO | WO03077996 A2 | 9/2003 | | |
| WO | WO2004096343 A2 | 11/2004 | | |
| WO | WO2010070494 A1 | 6/2010 | | |
| WO | WO2010076710 A1 | 7/2010 | | |
| WO | WO2011058462 A2 | 5/2011 | | |
| WO | WO2011112807 A1 | 9/2011 | | |

* cited by examiner

PATIENT INTERFACE HAVING ILLUMINATED PORTION

CROSS-REFERENCE TO RELATED APPLICATIONS

This patent application claims the priority benefit under 35 U.S.C. § 371 of international patent application no. PCT/IB2013/051642, filed Mar. 1, 2013, which claims the priority benefit under 35 U.S.C. § 119(e) of U.S. Provisional Application No. 61/607,145 filed on Mar. 6, 2012, the contents of which are herein incorporated by reference.

BACKGROUND OF THE INVENTION

1. Field of the Invention

The present invention generally relates to patient interface systems for supplying a flow of gas to the airway of a patient, and, more particularly, to patient interface systems having one or more illuminated portions. The invention further relates to coupling assemblies having one or more illuminated portions for use in patient interface systems.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation (NIV). It is also known to deliver continuous positive airway pressure (CPAP) or variable airway pressure, which varies with the patient's respiratory cycle, to treat a medical disorder, such as sleep apnea syndrome, in particular, obstructive sleep apnea (OSA), chronic obstructive pulmonary disease (COPD) or congestive heart failure (CHF).

Non-invasive ventilation and pressure support therapies involve the placement of a patient interface device, which is typically a nasal or nasal/oral mask, on the face of a patient to interface the ventilator or pressure support system with the airway of the patient so that a flow of breathing gas can be delivered from the pressure/flow generating device to the airway of the patient.

Typically, patient interface devices include a mask shell having a cushion attached to the shell that contacts the surface of the patient. The mask shell and cushion are held in place by a headgear that wraps around the head of the patient. The mask and headgear form the patient interface assembly. A typical headgear includes flexible, adjustable straps that extend from the mask to attach the mask to the patient.

Because such masks are typically worn for an extended period of time, a variety of concerns must be taken into consideration. For example, in providing CPAP to treat OSA, the patient normally wears the patient interface device all night long while he or she sleeps. One concern in such a situation is that the patient interface device is as comfortable as possible, otherwise the patient may avoid wearing the interface device, defeating the purpose of the prescribed pressure support therapy. It is also important that the interface device provide a tight enough seal against a patient's face without discomfort. A problem arises in that in order for the mask to maintain a seal without any undue gas leaks around the periphery of the mask, the mask may be compressed against the patient's face.

Typical CPAP patient interface masks have a plastic tube or conduit that transports air from the CPAP device to the airway of the user. As CPAP therapy is commonly used to treat sleep disorders, such therapy is typically administered to the user while they are in low light or no light conditions. If the user awakes from sleep and need to leave the bed (e.g., without limitation, to use the bathroom), the user typically must disconnect the tube before leaving the bed. When the user returns to go back to sleep, it may be difficult to locate components of the system (i.e., patient interface, conduit, etc.) and also to see where to reconnect the conduit in order to return to the therapy. In order to locate components and/or to reconnect the conduit, a light may be needed which would tend to interfere with the user's ability to fall back asleep and or disturb the sleep of others nearby.

SUMMARY OF THE INVENTION

Accordingly, it is an object of the present invention to provide an improved cushion for use in a patient interface device that overcomes the shortcomings of conventional cushions. As an aspect of the invention, a coupling for use in a system for communicating a flow of gas from a pressure generating device to an airway of a patient is provided. The coupling comprises a first portion adapted to be coupled in fluid communication with the pressure generating device and a second portion selectively coupled to the first portion, the second portion adapted to be coupled in fluid communication with the airway of the patient. At least one of the first portion and the second portion comprises an illuminated portion adapted to be visible to a patient when the first and second portions are uncoupled. The illuminated portion is adapted to be not visible to a user when the first and second portions are coupled.

The illuminated portion may be adapted to be visible to a patient when the first and second portions are partially uncoupled. The illuminated portion may comprise a photoluminescent material. The illuminated portion may comprise an electrically powered light source. The electrically powered light source may be disposed in the first portion and the illuminated portion may be adapted to be powered by a source disposed on or in the pressure generating device. The electrically powered light source may be disposed on one of the first portion and the second portion and powered by a battery also disposed on the one of the first portion and the second portion. One of the first and second portions may comprise a switch element structured to detect partial or complete uncoupling of the first and second portions and, responsive thereto, provide electric power to the light source.

As another aspect of the invention, a patient circuit for use in a system for delivering a flow of gas to a patient is provided. The patient circuit comprises a patient interface and a conduit. The conduit includes a first end adapted to be coupled to a pressure generating device and an opposite second end selectively coupled to the patient interface. At least one of the patient interface and the second end of the conduit comprises an illuminated portion. The illuminated portion is adapted to be visible to a patient when the patient interface and the second end of the conduit are uncoupled and adapted to be not visible to a user when the patient interface and second end portion is coupled.

The illuminated portion may be adapted to be visible to a patient when the patient interface and the second end of the conduit are partially uncoupled. The illuminated portion may comprise a photoluminescent material. The illuminated portion may comprise an electrically powered light source. The electrically powered light source may be disposed in the second end of the conduit and the illuminated portion may be adapted to be powered by a source disposed on or in the pressure generating device. The electrically powered light source may be disposed on one of the patient interface and the second end of the conduit and the electrically powered light source may be powered by a battery also disposed on the one of the patient interface and the conduit. One of the patient interface and the second end of the conduit may comprise a switch element structured to detect partial or complete uncoupling of the patient interface and the conduit and, responsive thereto, provide electric power to the light source. The illuminated portion may be disposed within the conduit and the illuminated portion may be adapted to be illuminated by a light source disposed on or in the pressure generating device which communicates light within the conduit. The illuminated portion may be disposed on an end surface of the conduit and the illuminated portion may be adapted to be illuminated by a light source disposed on or in the pressure generating device which communicates light to the illuminated portion via a number of fiber optic filaments.

At least one of the patient interface and the conduit may comprise a selectively illuminated portion formed in, on or coupled to the at least one of the patient interface and the conduit, the selectively illuminated portion being structured to awaken a user interfaced with the patient interface. The selectively illuminated portion may be structured to be illuminated in response to detecting a predetermined condition within the system. The predetermined condition may be selected from one or more of the group consisting of a leak in the flow of pressurized gas provided to the patient, a low level of treatment gas, and a low level in a humidifier reservoir. The selectively illuminated portion may be structured to be illuminated at a predetermined time adapted to be selected by the user.

As yet another aspect of the invention, a system for providing a pressurized flow of gas to the airway of a patient is provided. The system comprises a pressure generating device and a patient circuit. The patient circuit comprises a patient interface and a conduit. The conduit includes a first end coupled to the pressure generating device and an opposite second end selectively coupled to the patient interface. At least one of the patient interface and the second end of the conduit comprises an illuminated portion. The illuminated portion is adapted to be visible to a patient when the patient interface and the second end of the conduit are uncoupled and the illuminated portion is adapted to be not visible to a user when the patient interface and second end portion are coupled.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE EXEMPLARY EMBODIMENTS

Figure 1:
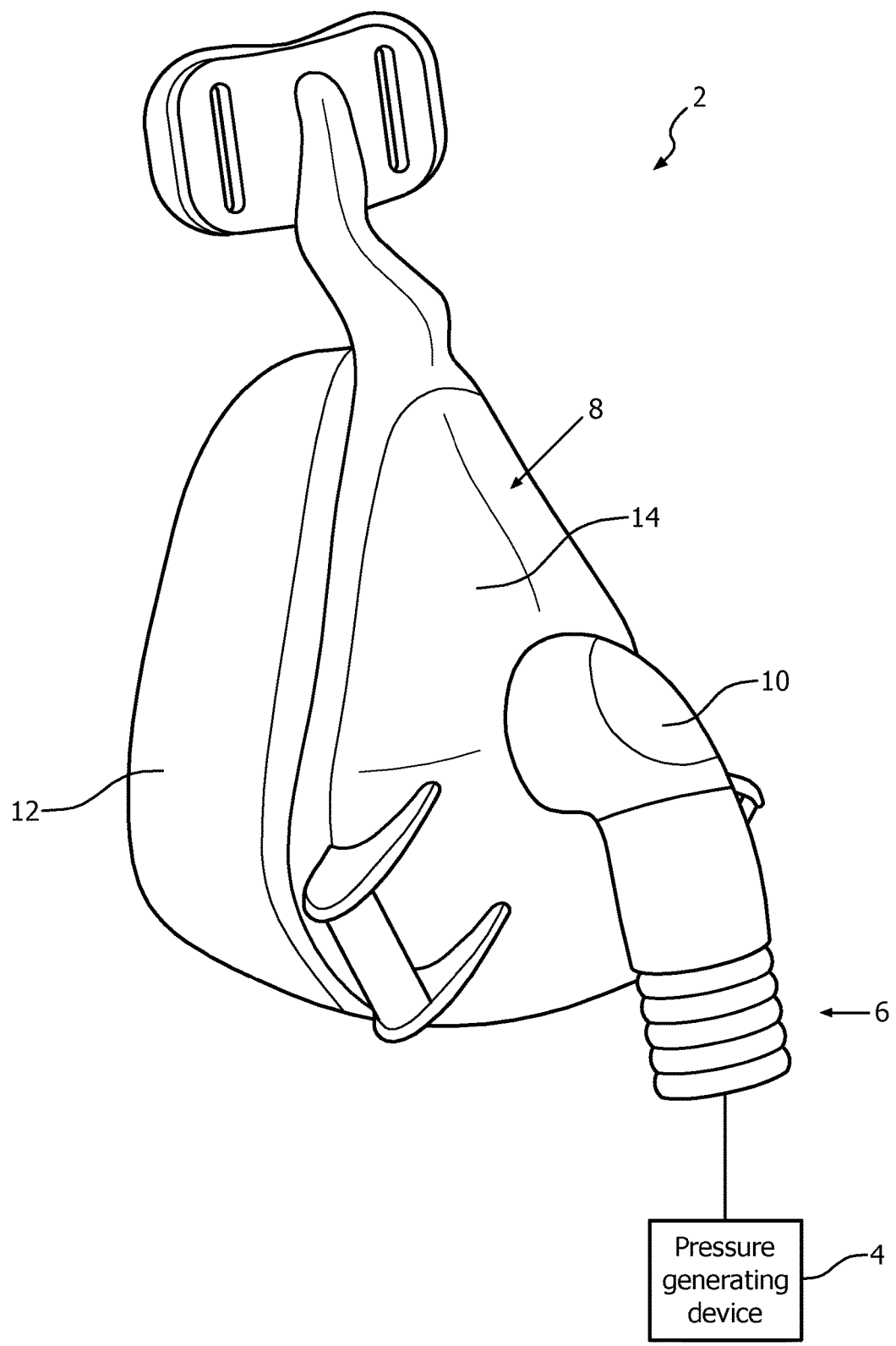
FIG. 1 is a front isometric view of a patient interface and a portion of a conduit according to the principles of the present invention shown connected to a gas flow/pressure generating system (shown schematically) to form an exemplary embodiment of a patient interface system.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As employed, herein, the statement that two or more parts or components are "coupled" together shall mean that the parts are joined or operate together either directly or through one or more intermediate parts or components.

As employed herein, the statement that two or more parts or components "engage" one another shall mean that the parts exert a force against one another either directly or through one or more intermediate parts or components.

As employed herein, the term "number" shall mean one or an integer greater than one (i.e., a plurality) and the singular form of "a", "an", and "the" include plural referents unless the context clearly indicates otherwise.

A system 2 adapted to provide a regimen of respiratory therapy to a patient according to one exemplary embodiment of the invention is generally shown in FIG. 1. System 2 includes a pressure generating device 4 (shown schematically), a delivery conduit 6 (shown partially schematically), and a patient interface device 8 having a fluid coupling conduit 10. Pressure generating device 4 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and auto-titration pressure support devices.

Delivery conduit 6 is structured to communicate the flow of breathing gas from pressure generating device 4 to patient interface device 8 through fluid coupling conduit 10, which in the illustrated embodiment is an elbow connector. Delivery conduit 6 and patient interface device 8 are often collectively referred to as a patient circuit.

A BiPAP® device is a bi-level device in which the pressure provided to the patient varies with the patient's respiratory cycle, so that a higher pressure is delivered during inspiration than during expiration. An auto-titration pressure support system is a system in which the pressure varies with the condition of the patient, such as whether the patient is snoring or experiencing an apnea or hypopnea. For present purposes, pressure/flow generating device 4 is also referred to as a gas flow generating device, because flow results when a pressure gradient is generated. The present invention contemplates that pressure/flow generating device 4 is any conventional system for delivering a flow of gas to an airway of a patient or for elevating a pressure of gas at an airway of the patient, including the pressure support systems summarized above and non-invasive ventilation systems.

In the illustrated exemplary embodiment, patient interface device 8 is depicted as a nasal/oral mask which includes a patient sealing assembly 12 coupled to a generally rigid frame member 14 which is coupled to conduit 6 via fluid coupling conduit 10. However, it is to be appreciated that other types of patient interface devices, such as, without limitation, a nasal mask or a full face mask, which facilitates the delivery of the flow of breathing gas to the airway of a patient, may be substituted for patient interface device 8 while remaining within the scope of the present invention. It is also to be appreciated that conduit 6 may be directly coupled to patient interface device 8 without the use of any intermediary coupling, such as conduit 10.

Figure 2:
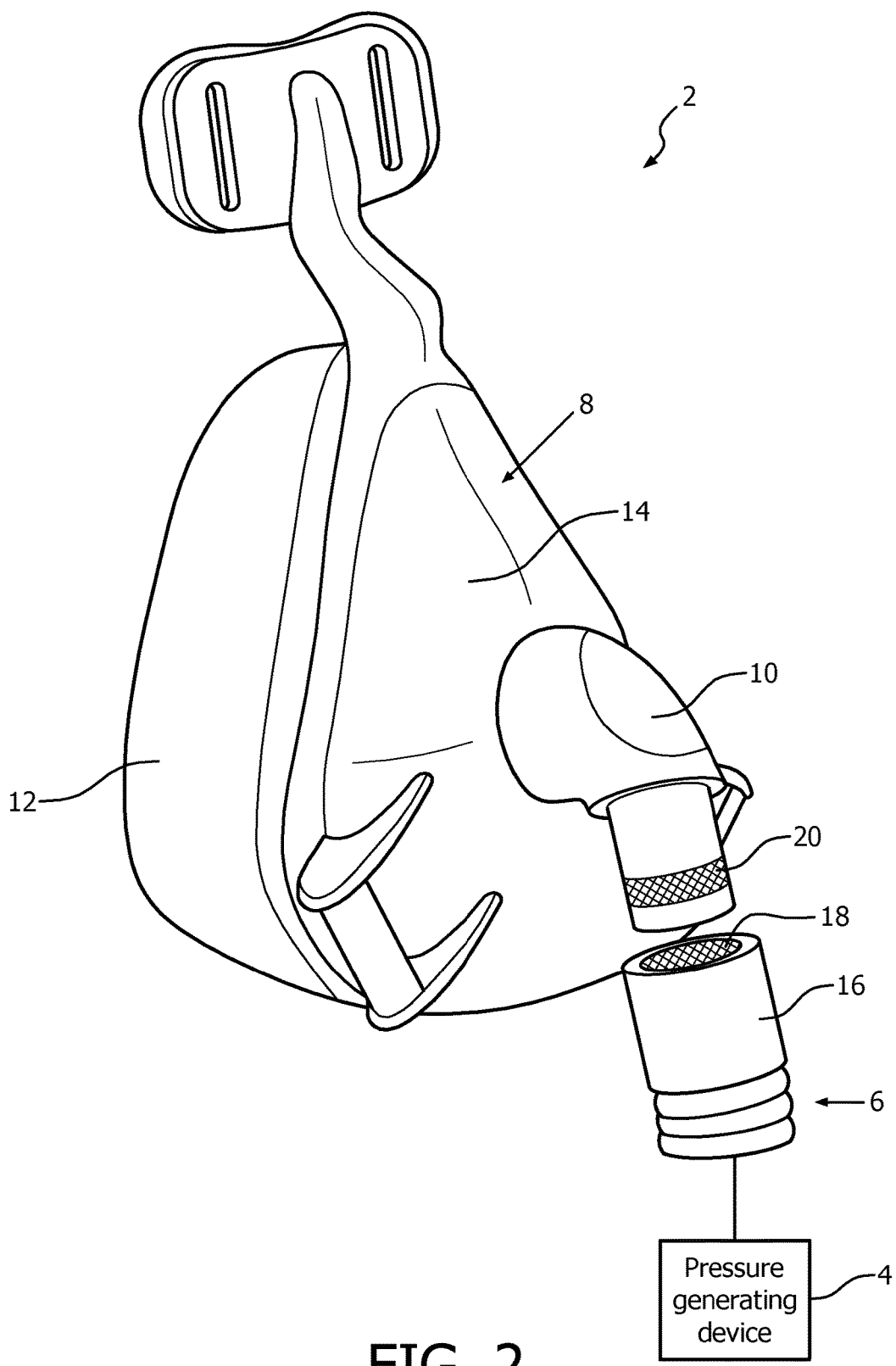
FIG. 2 is another view of the system of FIG. 1 with the conduit uncoupled from the patient interface.

FIG. 2 shows system 2 of FIG. 1 with an end 16 of delivery conduit 6 uncoupled from conduit 10 of patient interface device 8, such as would commonly occur when a patient undergoing CPAP therapy awakens during the night and gets out of bed to use the restroom. In order to assist in locating and recoupling end 16 of delivery conduit 6 in a darkened room, an illuminated portion 18 (shown hatched for clarity) is provided on end 16. As shown in the coupled, and uncoupled views of FIGS. 1 and 2 respectively, illuminated portion 18 is positioned such that it is visible when end 16 is uncoupled (FIG. 2) from patient interface device 8, yet not visible to a user when end 16 is coupled (FIG. 1) to patient interface device 8. Additionally, illuminated portion 18 may also be positioned so as to be visible to a user when end 16 is partially uncoupled from patient interface device 8, thus providing an indicator of incomplete or improper coupling. In the exemplary embodiment shown in FIG. 2, illuminated portion 18 comprises a photoluminescent material, and thus does not require any power supply. However, as will be readily appreciated from the further disclosure herein, illuminated portion may be formed from other illuminated or selectively illuminatable materials and or structures without varying from the scope of the present invention.

As shown in the exemplary embodiment of FIG. 2, the corresponding coupling portion of patient interface device 8 may also be provided with an illuminated portion 20 (shown hatched for clarity). Similar to illuminated portion 18, illuminated portion 20 is provided to assist in locating and coupling conduit 10 of patient interface device 8 to end 16 of conduit 6, and thus is also positioned to only be visible to a user when end 16 is uncoupled, or potentially partially uncoupled, from patient interface device 8.

Figure 3:
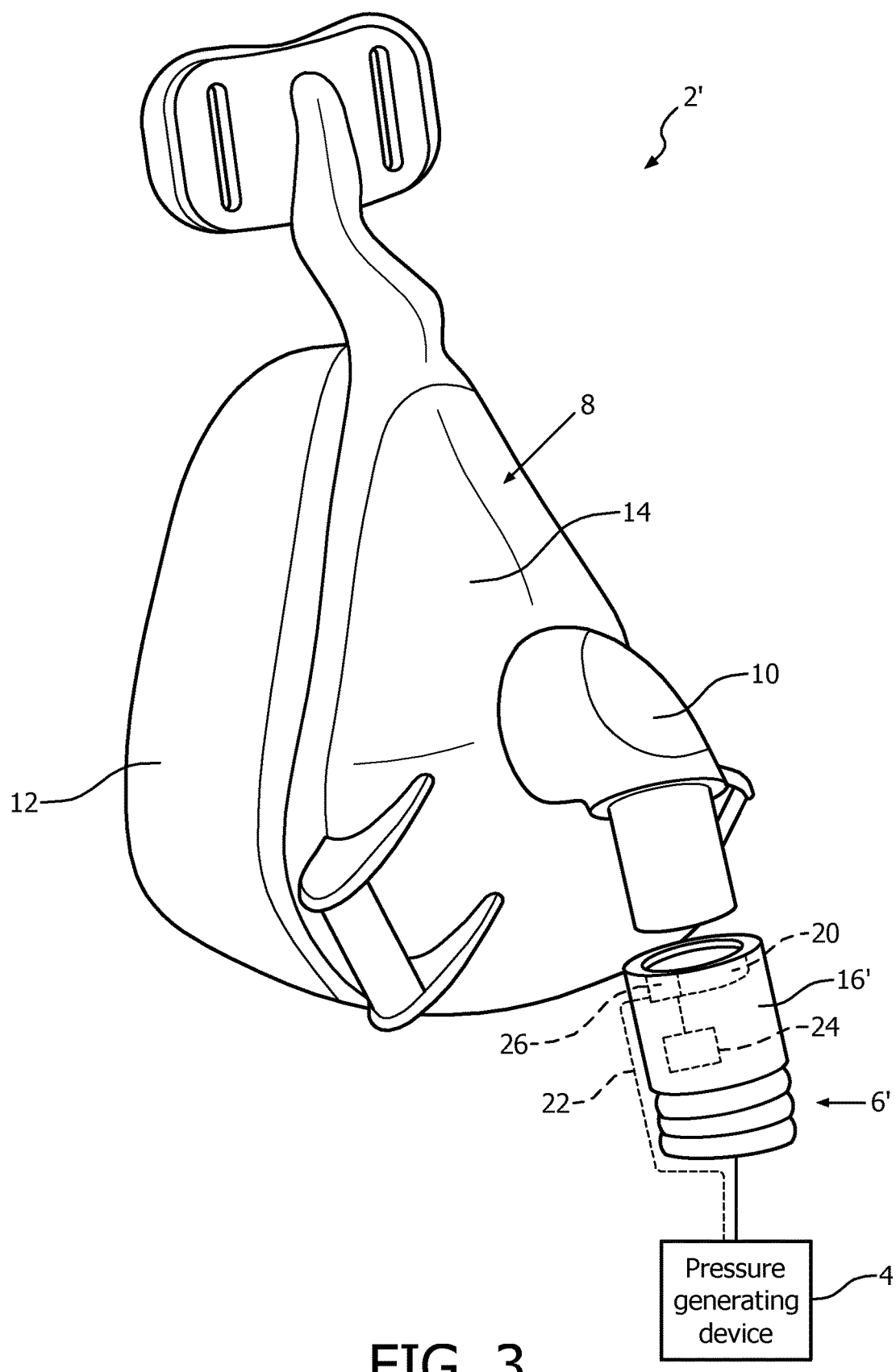
FIG. 3 is a view of another patient interface system similar to the system of FIGS. 1 and 2 but showing another exemplary embodiment of a conduit according to the principles of the present invention uncoupled from the patient interface.

FIG. 3 shows another exemplary embodiment of a system 2' in accordance with the present invention that is arranged in a similar manner as system 2, aside from instead of having an illuminated portion comprising an illuminated material which does not require a power source, an electrically powered illuminated portion 20 (shown schematically in dashed line) is provided on end 16' of conduit 6'. Electrical power may be provided to illuminated portion 20 either by an electrical power supply (not numbered) disposed in pressure generating device 4 and transmitted via wires 22 (shown schematically in dashed line) or other suitable means disposed on or in conduit 6, or alternately by a power supply 24 (shown schematically in dashed line, e.g., without limitation, batteries) disposed in or on conduit 6'.

In contrast to illuminated portions 18 and 20 which in the exemplary embodiment are formed from photoluminescent material, and thus are always illuminated, electrically powered illuminated portion 20 may either be constantly illuminated or may be selectively illuminated, such as controlled by a switching mechanism 26 (shown schematically in dashed line) disposed in or on end 16' which breaks the electrical communication between illuminated portion 20 and its power supply. Such break in the electrical communication between the power supply and illuminated portion 20 may be triggered by either complete or partial coupling of end 16' and conduit 10 of patient interface 8 depending on the application.

In embodiments where a switching mechanism is provided, illuminated portion 20 may be disposed in either a location not visible to the patient or in a location visible to the patient when end 16' is coupled to patient interface device 8, as illuminated portion 20 would not be noticed and thus not undesirable to a user attempting to sleep when switched off. In embodiments where inclusion of a switching mechanism is not desired (e.g., without limitation, due to cost, complexity), illuminated portion 20 is disposed in a similar manner as illuminated portion 18 so as to not be visible to a user when end 16' is coupled to patient interface device 8.

Figure 4:
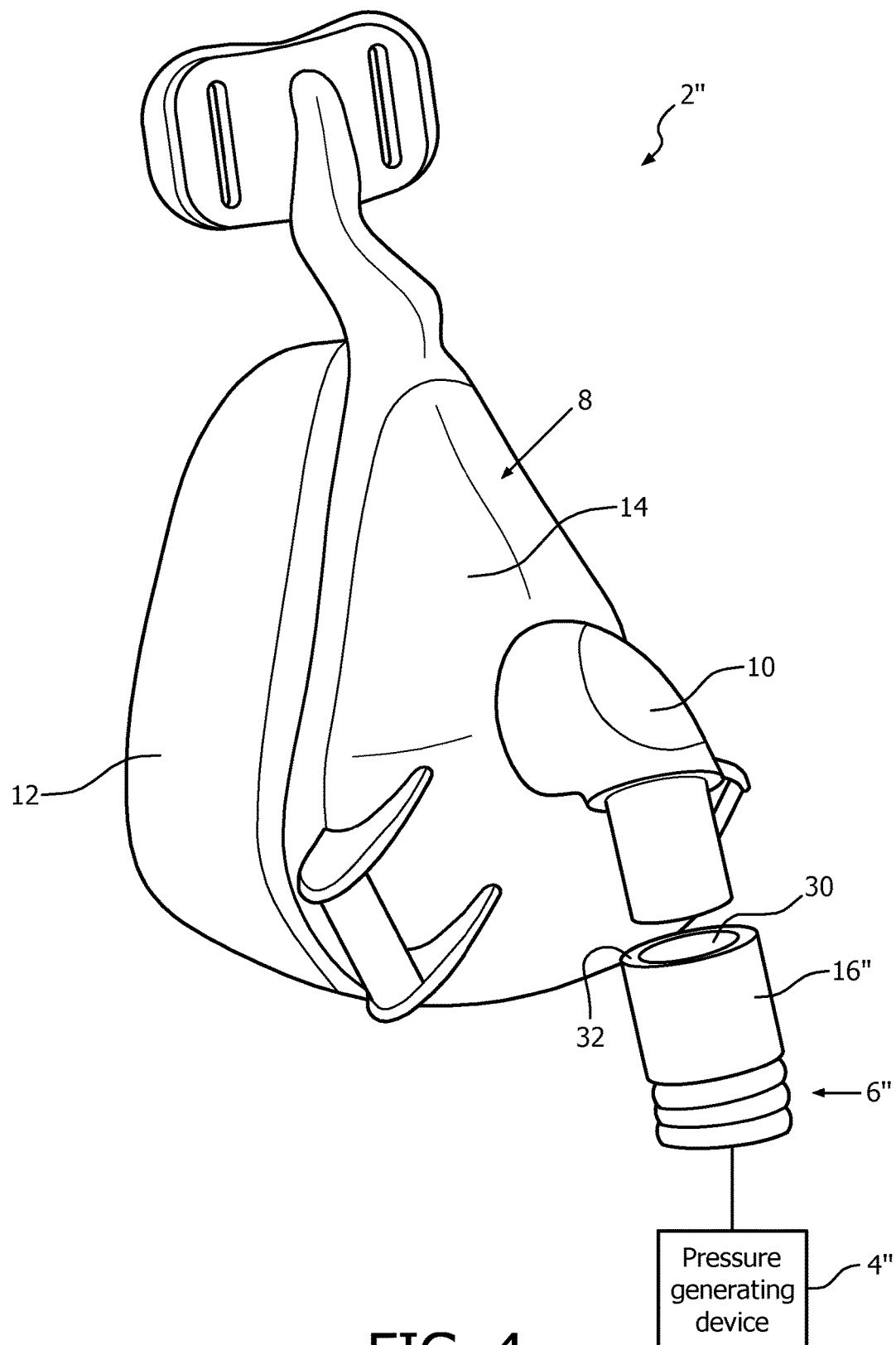
FIG. 4 is a view of yet another patient interface system similar to the system of FIGS. 1-3 but showing yet another exemplary embodiment of a conduit according to the principles of the present invention uncoupled from the patient interface.

FIG. 4 shows yet another exemplary embodiment of a system 2" in accordance with the present invention that is arranged in a similar manner as systems 2 and 2', except end 16" includes an illuminated portion (not numbered) that is illuminated by source of illumination external to conduit 6". In the particular exemplary embodiment shown in FIG. 4, such external source of illumination (not numbered) is provided in or on pressure generating device 4" and communicated in or on conduit 6" to end 16". For example, without limitation, an interior portion 30 of end 16" may be illuminated by a light source projecting inside conduit 6". As another example, an end surface 32 of end 16" may be illuminated by communicating a light source via fiber optic filaments disposed on or in conduit 6". As with the embodiments described in conjunction with system 2' of FIG. 3, the lighted portion of end 6" of system 2" may also be switched depending on the desired application.

Figure 5:
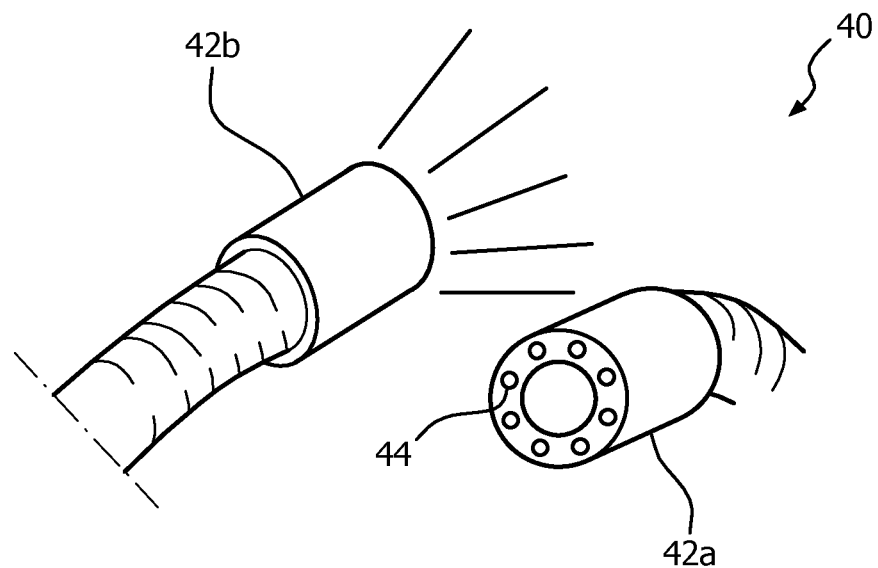
FIG. 5 is an isometric view of an exemplary embodiment of a coupling according to the principles of the present invention shown in an uncoupled position.

FIG. 5 shows an exemplary embodiment of a coupling 40 (shown uncoupled) in accordance with the present invention at which point two portions of a conduit 42a and 42b may be selectively coupled by a user. In order to assist a user in locating and recoupling coupling 40 in a darkened room, one or both of the ends (not numbered) of portions 42a and 42b may be provided with a number of LEDs or other suitable selectively illuminatable elements 44 which may be powered from a local power source (e.g., without limitation, batteries) or from a remote power source disposed a distance from coupling 40 (e.g., without limitation, on a pressure generating device to which one of portions 42a and 42b is coupled).

It is to be appreciated that the concepts disclosed herein may be readily applied to couplings disposed anywhere along a conduit where the inclusion of illuminated, or selectively illuminatable portions would be desirable and as such are not limited to the positions illustrated herein. Additionally, it is to be appreciated that the male/female coupling arrangements illustrated herein are provided for example purposes only and may be reversed without varying from the scope of the present invention. Also, it is to be appreciated that the present invention is not intended to be limited to such male/female coupling arrangements, but instead it is contemplated that the concepts described herein may be applied to other suitable coupling mechanisms without varying from the scope of the present invention.

Figure 6:
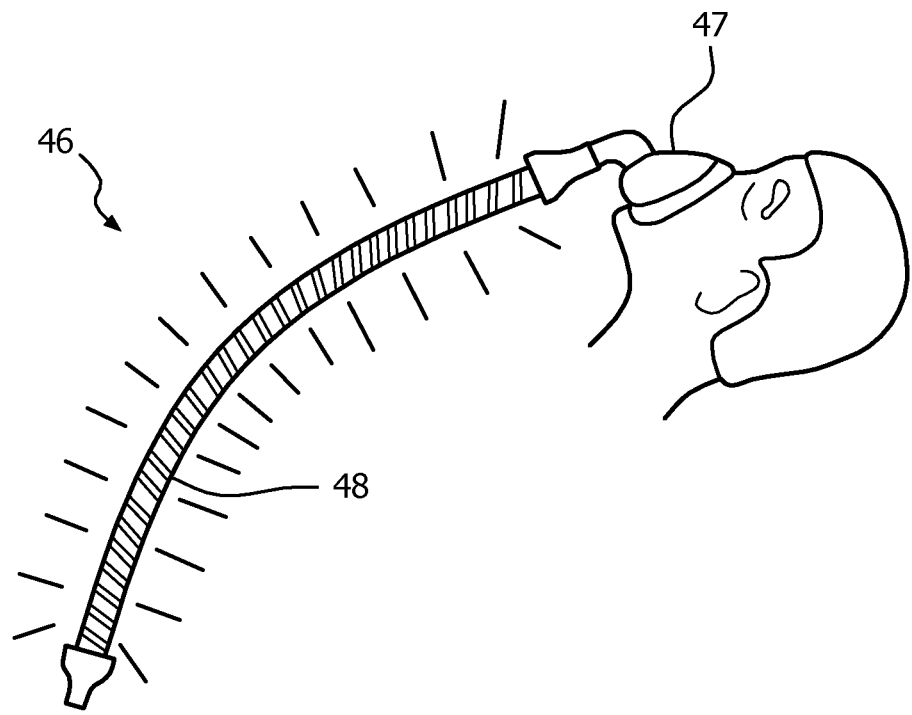
FIG. 6 is a side view of an exemplary embodiment of a patient circuit according to the principles of the present invention shown disposed on the head of a patient.

FIG. 6 shows a side view of an exemplary embodiment of a patient circuit 46 according to the principles of the present invention which includes a patient interface 47 and a conduit 48 coupled thereto. Unlike the previous embodiment in which generally an end portion of a conduit was selectively illuminatable, conduit 48 is generally selectively illuminatable along its entire length by providing selectively illuminatable elements (not numbered) along conduit 48. Such selectively illuminatable elements may be provided on, in, or otherwise suitably positioned with respect to conduit 48 and may include, for example, without limitation, LEDs, fiber optic elements or other suitable elements. It is to be appreciated that such illumination of a larger portion of a conduit may be used to help locate and assist in recoupling of selected portions of the conduit and/or may be useful in alerting the user of particular circumstances or conditions, as will discussed in greater detail below.

Figure 7A:
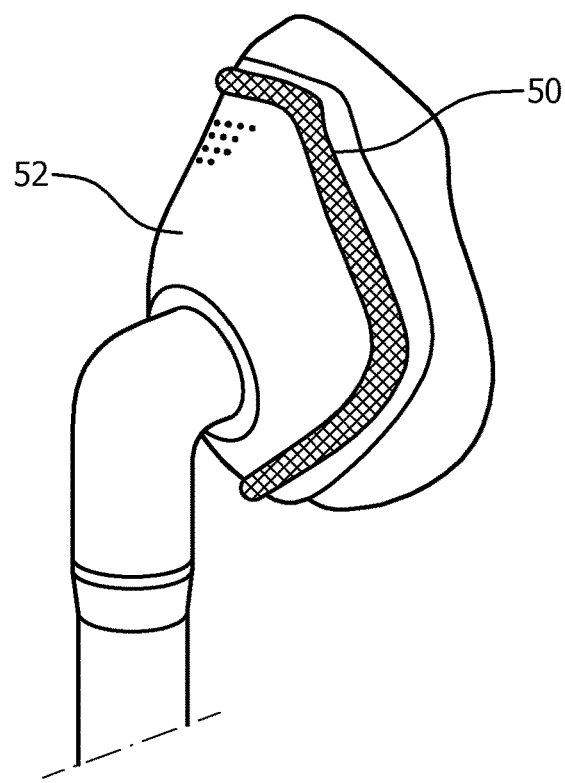
FIG. 7A is an isometric view of another exemplary embodiment of a patient interface having a selectively illuminatable portion according to the principles of the present invention.

FIG. 7A shows another use of an illuminated portion, particularly a selectively illuminated portion 50 on a patient interface 52 according to the principles of the present invention. Selectively illuminated portion 50 is formed from a number of LEDs or other suitable illuminatable elements which may be electrically powered via an energy storage means (e.g., without limitation, a battery) provided on patient interface 52 or via a power supply provided separately from patient interface 52 (e.g., without limitation, on a pressure generating device) and electrically coupled to selectively illuminated portion 50 via one or more switching means. Power to selectively illuminated portion 50 is controlled via a switching means (not shown) provided between portion 50 and the energy storage means. In applications where portion 50 is powered via a battery or other similar local energy storage means, such switching means may be controlled via a wireless or other suitable connection. Through the use of such switching means, selectively illuminated portion 50 may be illuminated or switched off as desired dependent on particular operating conditions.

Selectively illuminated portion 50 is positioned generally near the eyes of a user so as to be noticeable by a user on which patient interface 52 is disposed. Such arrangement provides for selectively illuminated portion 50 to be used as an alarm to gently awaken a user in particular circumstances. For example, selectively illuminated portion 50 may be used as a wake-up alarm by being coupled to a timing device that may be preprogrammed to activate selectively illuminated portion 50 at a predetermined time that may be selected by a user. As another example, selectively illuminated portion 50 may also be used as an alarm to awaken a user in response to certain predetermined conditions within the patient interface system which may require immediate attention. Such details may include, for example, without limitation, a leak in the flow of pressurized gas provided to the patient, a low level of treatment gas, or a low level in a humidifier reservoir. Additionally, selectively illuminated portion 50 may also be used to help locate patient interface 52 in a darkened room, by illuminating portion 50 when patient interface 52 is removed from a user.

Figure 7B:
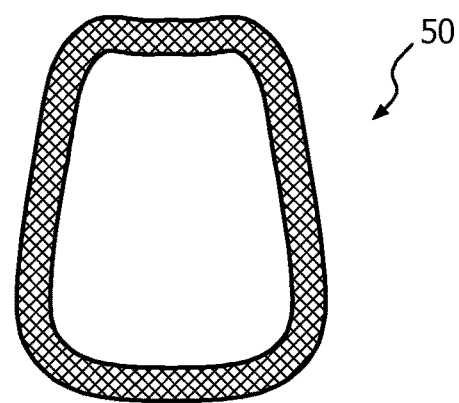
FIG. 7B is a front elevational view of the selectively illuminatable portion of the patient interface of FIG. 5A.

In the exemplary embodiment of FIG. 7A, selectively illuminated portion 50, shown generally in FIG. 7B, is formed separately from patient interface 52 and coupled either permanently or selectively thereto. Such arrangement provides for selectively illuminated portion 50 to be readily retrofit to existing patient interfaces. It is to be appreciated that coupling of selectively illuminated portion 50 to patient interface 52 may be accomplished via any suitable coupling means without varying from the scope of the present invention. The present invention also contemplates that selectively illuminated portion 50 may be formed as an integral portion of patient interface 52. Regardless of whether formed separately from, or integrally with, patient interface 52, it is to be appreciated that one or more of the quantity, size, shape, color or intensity of selectively illuminated portion 50 may be varied without varying from the scope of the present invention.

Figure 8:
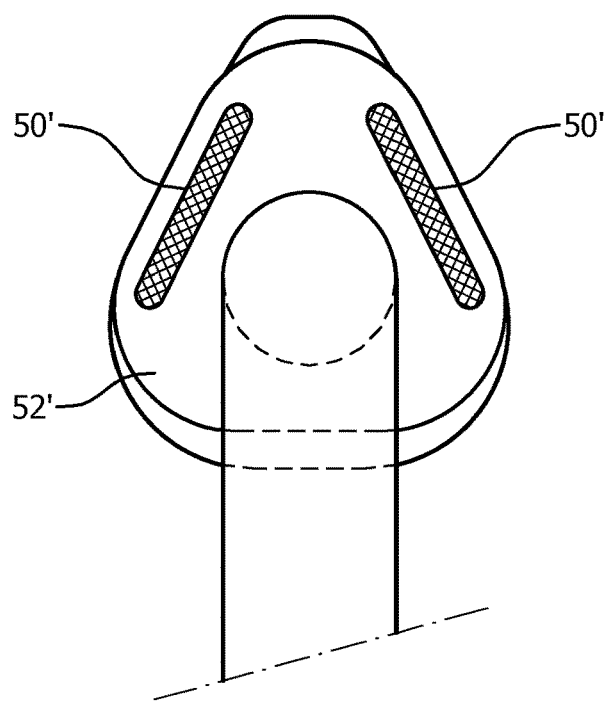
FIG. 8 is a front elevational view of yet another exemplary embodiment of a patient interface having a selectively illuminatable portion according to the principles of the present invention.
Figure 9:
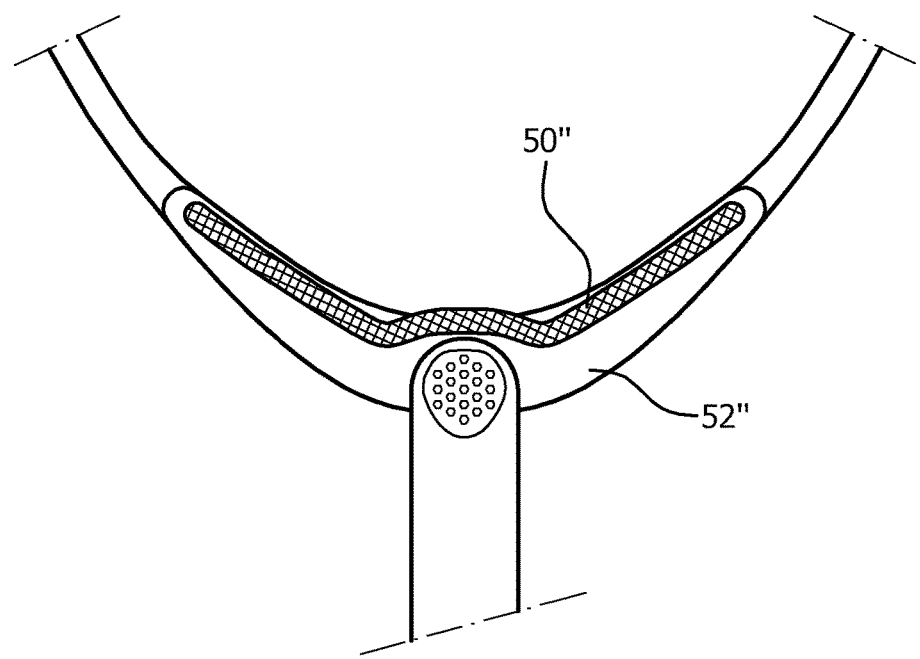
FIG. 9 is a front elevational view of a further exemplary embodiment of a patient interface having a selectively illuminatable portion according to the principles of the present invention.

FIGS. 8-16C show additional exemplary embodiments of patient interfaces including selectively illuminated portions according to the principles of the present invention. More particularly, FIGS. 8 and 9 show examples similar to that of FIGS. 7A and 7B in that both embodiments include a patient interface 52' and 52" having selectably illuminatable portions 50' and 50" disposed on, in or coupled thereto in positions that would be readily apparent to a user upon which either of patient interfaces 52' or 52" are disposed.

Figure 10:
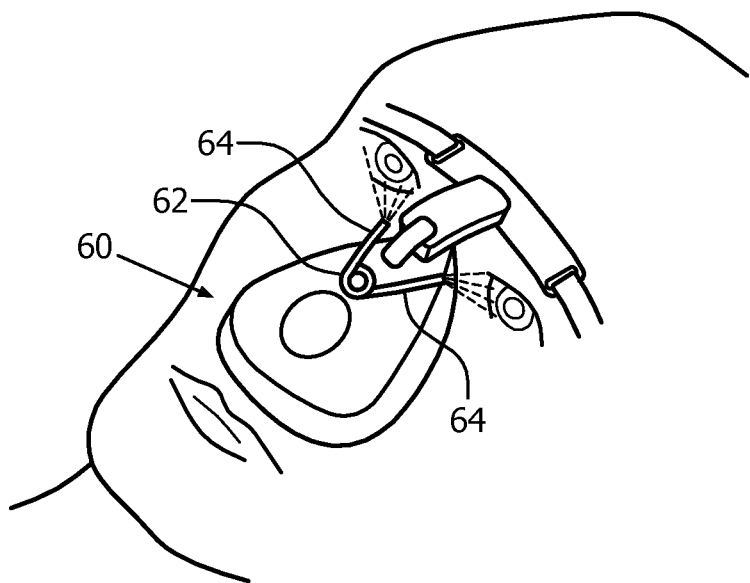
FIG. 10 is an isometric view of another exemplary embodiment of a patient interface according to the principles of the present invention disposed on the face of a patient.

FIG. 10 shows an exemplary embodiment of a patient interface 60 which employs a light source 62 (such as an LED) disposed thereon which may be covered by a cover member (not shown). Light from light source 62 is selectively directed toward the eyes of a user via fiber optic elements 64, or other suitable elements, so as to generally illuminate the eyes of a user, and not those of anyone else nearby.

Figure 11:
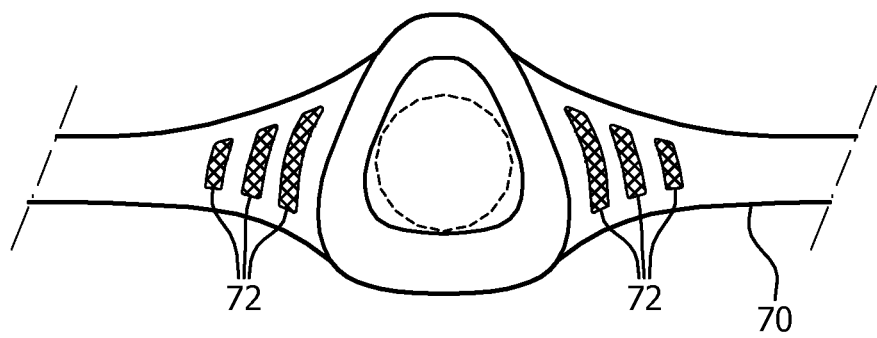
FIGS. 11-13 are elevational views of the patient side of further exemplary embodiments of patient interfaces according to the principles of the present invention.

FIG. 11 shows an exemplary embodiment of the present invention in which the patient interface is a minimal contact nasal frame or headgear 70 that utilizes multiple selectably illuminatable elements 72 on the patient side of the frame which may be selectably illuminatable in different patterns, colors, and/or intensities to provide different wake-up experiences to a user.

Figure 12:
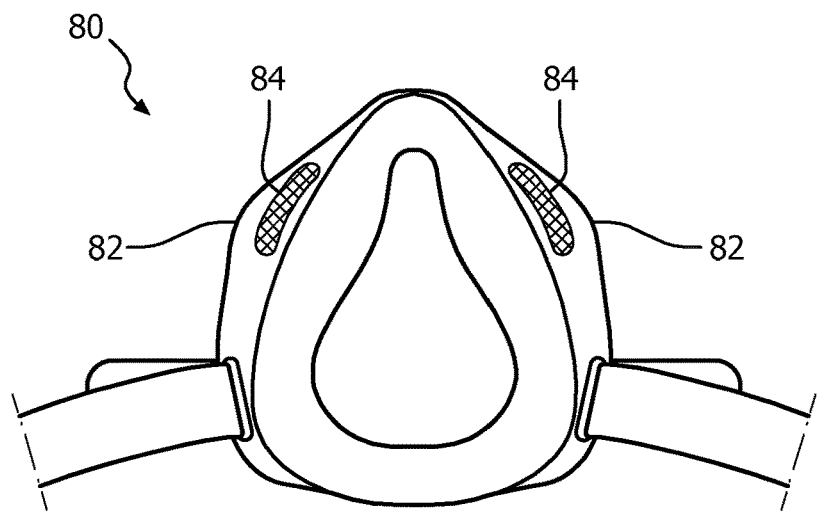

FIG. 12 shows an exemplary embodiment of the present invention in which the patient interface is a traditional nasal or full face mask 80 that includes faceplate extension 82 having selectably illuminatable elements 84 disposed thereon in the user's field of view. Such placement generally allows for the user's eyes to be selectably illuminated while shielding the light from any else nearby.

Figure 13:
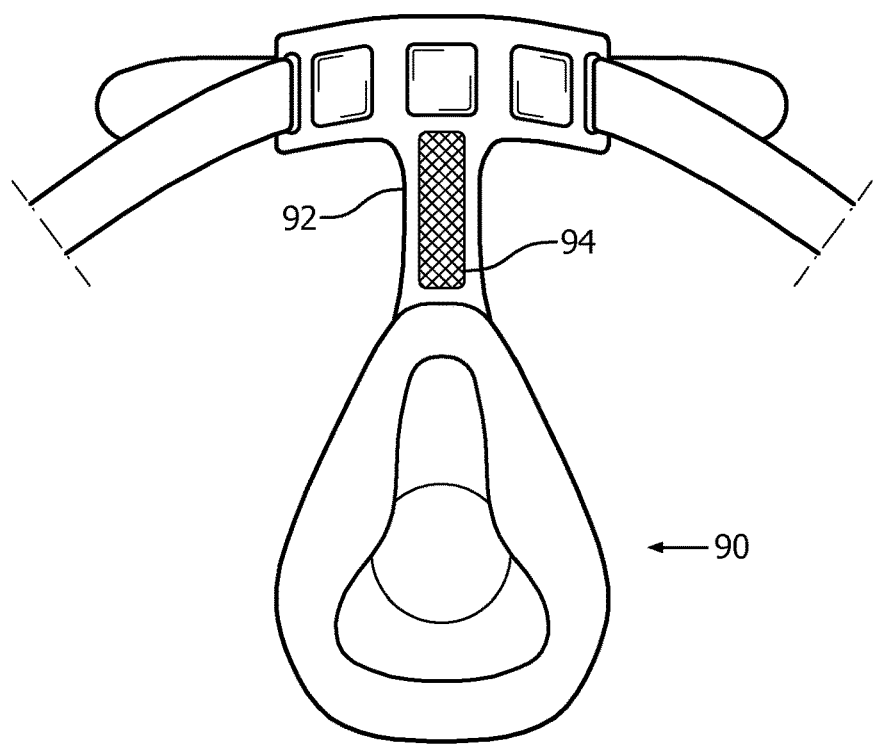

FIG. 13 shows an exemplary embodiment of the present invention in which the patient interface is a traditional nasal or full face mask 90 that utilizes space behind a forehead arm 92 to house a selectably illuminatable element 94. When donned by a user, forehead arm 92 is generally disposed in the user's field of vision enough to provide a wake-up function.

Figure 14A:
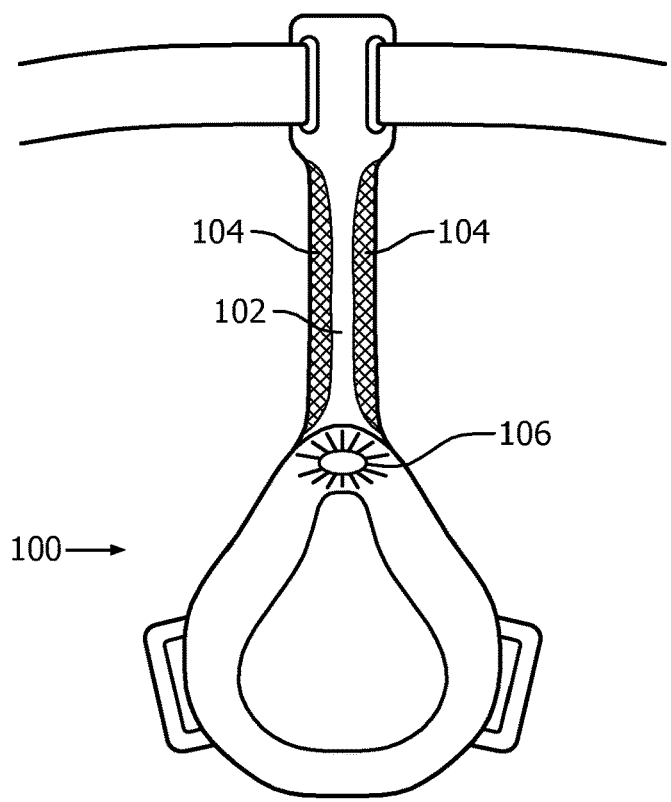
FIGS. 14A and 14B, respectively, are patient side, and side elevational views of yet another patient interface according to the principles of the present invention.
Figure 14B:
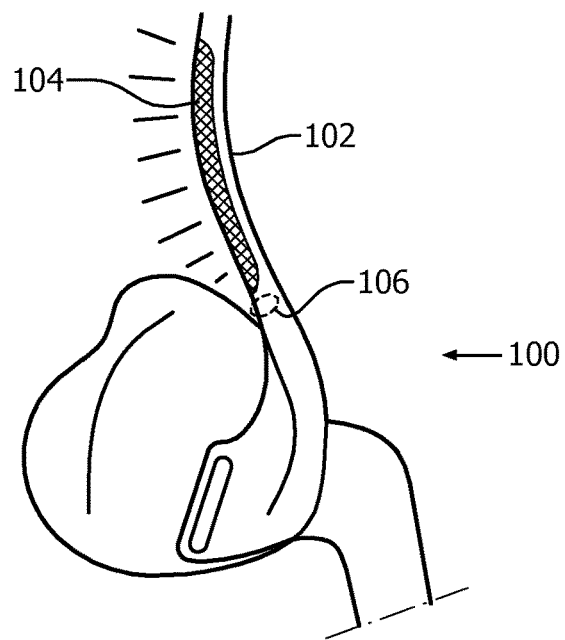

FIGS. 14A and 14B, respectively, show elevational vies of the patient side and side of a patient interface 100 according to the present invention having at least a forehead arm 102 formed from a clear polymer with textured areas 104 formed therein to highlight certain areas of the mask. A selectably illuminatable light source 106, such as an LED, is provided in or near forehead arm 102. Light from the light source passes through the clear material, but the refractions that occur at the textured areas cause that area to 'glow'. In the exemplary embodiment of FIGS. 14A and 14B, texture was placed along forehead arm 102 in the line of sight of a user so that the glow from light source 106 can be used as a wake-up function. A benefit of such arrangement is that when the light source is turned off, the portion of the mask that would glow for a wake-up alarm is a textured clear polymer. The light source may be hidden in an aesthetically pleasing location where it perhaps is not as noticeable to a user or others.

Figure 15:
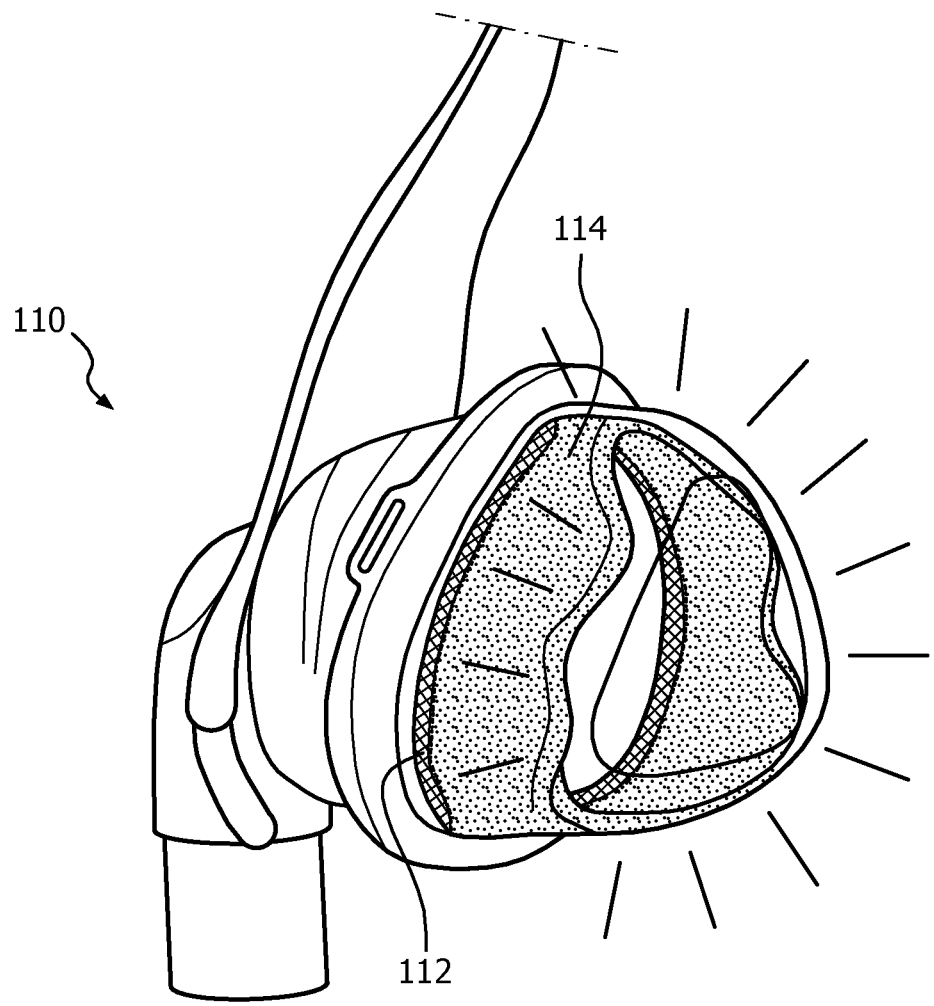
FIG. 15 is an isometric view of the patient side of another exemplary embodiment of a patient interface according to the principles of the present invention.

FIG. 15 shows an exemplary embodiment of a patient interface 110 according to the present invention which utilizes a selectably iluminatable element 112 disposed adjacent a cushion 114 which includes a generally clear, flexible housing having a generally clear gel disposed therein. When selectably illuminatable element 112 is illuminated, the gel housed within, and thus the majority of cushion 114, is generally illuminated in a manner that can be used for a wake-up or locating application.

Figure 16A:
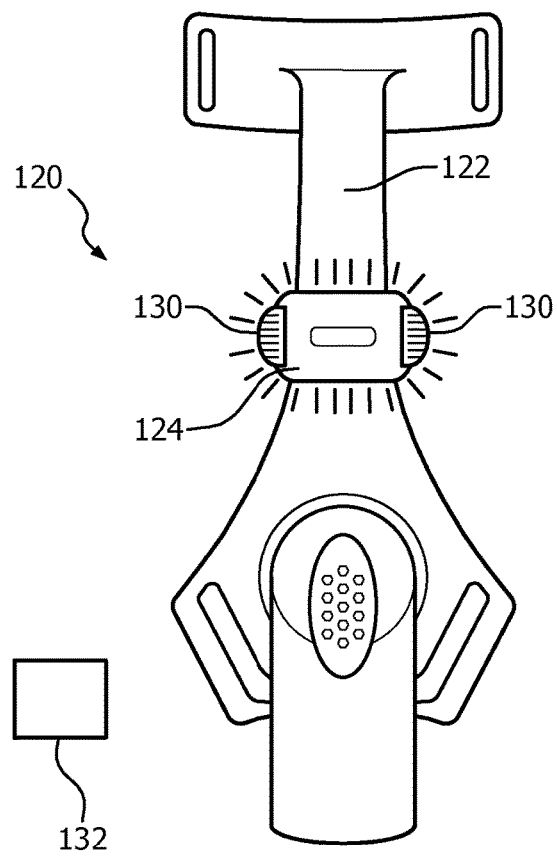
FIG. 16A is an elevational view of the front side of yet another exemplary embodiment of a patient interface according to the principles of the present invention.
Figure 16B:
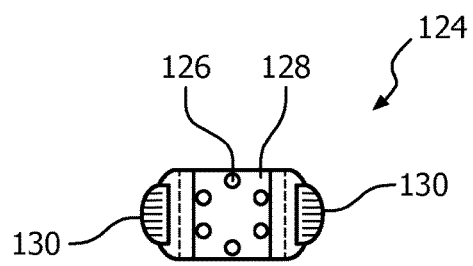
FIG. 16B is an elevational view of the patient side of a portion of the patient interface of FIG. 16A.
Figure 16C:
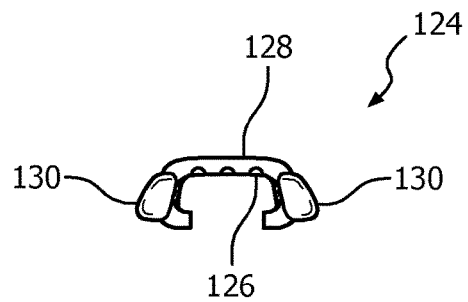
FIG. 16C is a bottom view of the portion of the patient interface of FIG. 16B.

FIGS. 16A-16C show another exemplary embodiment of a patient interface 120 having a forehead arm 122 formed from a generally clear material. Patient interface 120 includes a snap-on member 124 selectively coupled to forehead arm 122. As shown in FIG. 16B, snap-on member 124 includes a number of selectably illuminatable elements 126 disposed on or in a rear face 128 such that when snap-on member 124 is selectively coupled to forehead arm 122, selectably illuminatable elements 126 are directed toward a user upon which patient interface 120 is disposed, and thus may be used to provide an alarm function. Snap on-member 124 may further include finger grips 130 on either side which assist in removal or adjustment of member 124. The alarm function of such exemplary embodiment is provided via a wireless connection with a control unit 132 (shown schematically) which may be positioned a distance from patient interface 120. Selectably iluminatable elements 126 are powered by a small battery provided in member 124. It is to be appreciated that such arrangement provides a snap-on application that may be readily applied to existing mask applications with little to no modification. It is also to be appreciated that one or more of the size, shape, attachment location, number/type of selectably illuminatable elements may be varied without varying from the scope of the present invention.

Figure 17:
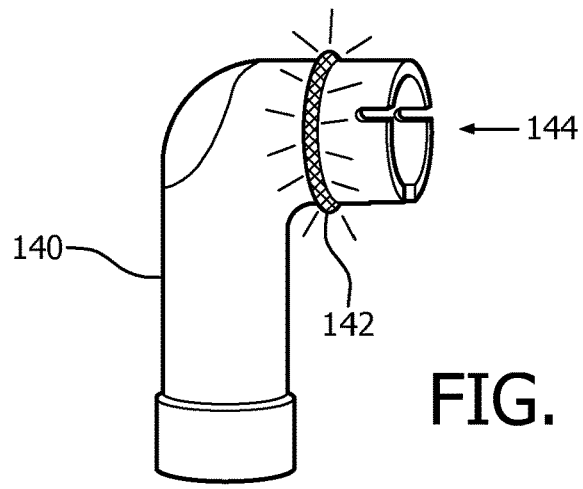
FIG. 17 is an isometric side view of an exemplary embodiment of a fluid coupling conduit according to the principles of the present invention.

FIG. 17 shows an exemplary embodiment of a fluid coupling conduit 140 according to the principles of the present invention which utilizes a selectively illuminatable element 142. Element 142 is generally ring-shaped and thus may simply slipped over an end 144 of conduit 140 that would then be coupled to a patient interface. Element 142 is then utilized in a similar manner as portion 50, as previously discussed in regard to FIGS. 7A and 7B.

Figure 18:
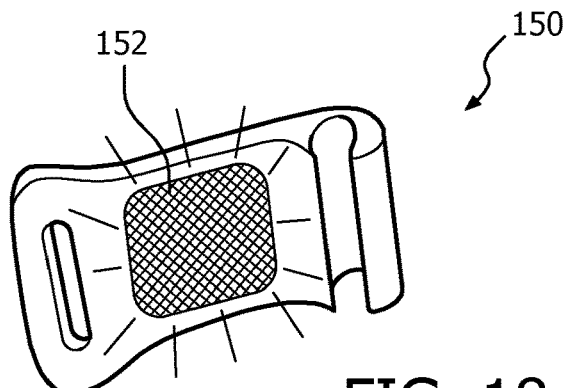
FIG. 18 is an isometric view of the patient side of an exemplary embodiment of a clip member according to the principles of the present invention.

FIG. 18 shows an exemplary embodiment of a clip member 150 according to the principles of the present invention which may be generally used in conjunction with a headgear (not shown) in securing a patient interface to the head of a user. Similar to the other embodiments disclosed herein, clip member 150 includes a selectably illuminatable portion 152 disposed to generally face a user when disposed on the head of a user. In the exemplary embodiment shown, selectably illuminatable portion 152 is formed from one or more LEDs powered by a battery disposed in clip member 150. Illumination of portion 152 is controlled via a wireless controllable switching mechanism which is also disposed within clip member 150.

Figure 19:
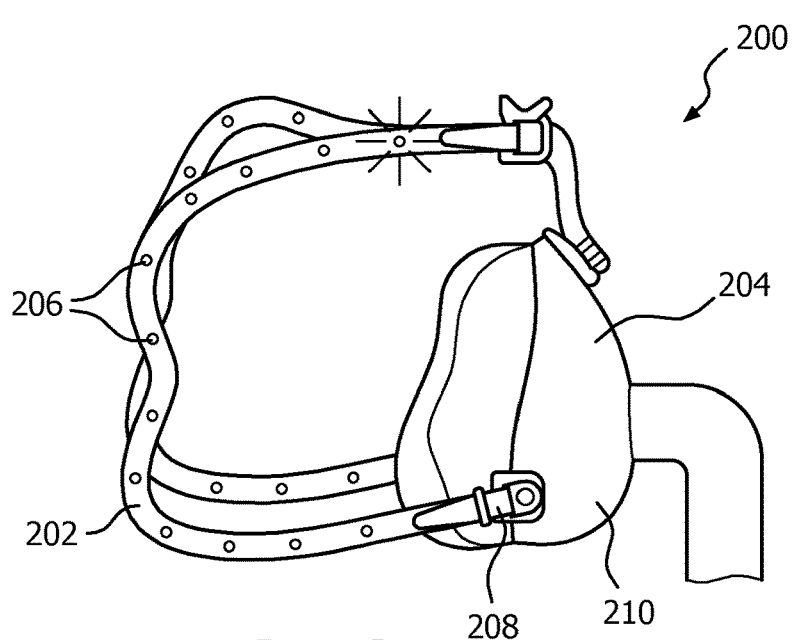
FIG. 19 is an isometric view of a patient interface including an illuminated headgear according to the principles of the present invention.

FIG. 19 shows an exemplary embodiment of a patient interface 200 according to a further embodiment of the present invention that includes a headgear 202 and a patient interface device 204. In this embodiment, one or more lights 206 or other illumination sources are disposed in headgear 202, which is typically a flexible material or combination of materials that wraps around a portion of the head. Lights 206 can be provided on any portion of the headgear, in any size, shape, pattern, color or combinations thereof.

In a further exemplary embodiment, patient interface 200 is configured such that when a headgear clip 208 is connected to mask 210, it breaks the connection for light 206, thereby turning off these light. That is, the lights are only activated if the headgear is removed from the patient or disconnected from the mask. This feature helps allows the patient to find the headgear when returning to a darkened room, and also helps the patient know the patient interface is assembled correctly.

The lights can be attached to the headgear or other portions of the patient interface by any process, such as adhesive, press fit, mechanical lock, Velcro™, overmolding, sewing, or woven. Also, the lights can have different colors so that when the light from two or more sources interact, they product a third color.

It is to be appreciated that the present invention is not intended to be limited to the mask, cushion, clip, or selectively illuminatable element shapes described herein, but instead may be employed with suitable similar structures of various other shapes or designs. Moreover, the lights or other illumination sources can have any quantity, size, shape, color or intensity without varying from the scope of the present invention.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A coupling for use in a system for communicating a flow of gas from a pressure generating device to an airway of a patient, the coupling comprising:
    a first portion disposed at an end of a flexible conduit adapted to be coupled in fluid communication with the pressure generating device; and
    a second portion selectively coupled to the first portion, the second portion adapted to be coupled in fluid communication with the airway of the patient, wherein at least one of the first portion and the second portion comprises an illuminated portion, wherein the illuminated portion is obstructed by the other one of the first portion and the second portion and thus is not visible to the patient when the first and second portions are coupled, wherein the illuminated portion is unobstructed and thus is visible to the patient when the first portion and the second portion are uncoupled, and wherein the illuminated portion comprises a photoluminescent material disposed circumferentially on a radially outward facing surface of the at least one of the first portion and the second portion.

2. A patient circuit for use in a system for delivering a flow of gas to a patient, the patient circuit comprising:
    a patient interface;
    a conduit having a first end and an opposite second end, the first end being adapted to be coupled to a pressure generating device; and
    a coupling as recited in claim 1 wherein the first portion is disposed at the second end of the conduit and the second portion is coupled to the patient interface.

3. A coupling for use in a system for communicating a flow of gas from a pressure generating device to an airway of a patient, the coupling comprising:
    a first portion disposed at an end of a flexible conduit adapted to be coupled in fluid communication with the pressure generating device; and
    a second portion selectively coupled to the first portion, the second portion adapted to be coupled in fluid communication with the airway of the patient, wherein at least one of the first portion and the second portion comprises an electrically powered light source, wherein the light source is obstructed by the other one of the first portion and the second portion and thus is not visible to the patient when the first and second portions are coupled, wherein the illuminated portion is unobstructed and thus is visible to the patient when the first portion and the second portion are uncoupled, and wherein one of the first and second portions comprise a switch element which is structured to detect partial or complete uncoupling of the first and second portions and, responsive thereto, provide electric power to the light source.

4. The coupling of claim 3, wherein the electrically powered light source is disposed in the first portion and wherein the illuminated portion is adapted to be powered by a source disposed on or in the pressure generating device.

5. The coupling of claim 3, wherein the electrically powered light source is disposed on one of the first portion and the second portion and powered by a battery also disposed on the one of the first portion and the second portion.

6. A patient circuit for use in a system for delivering a flow of gas to a patient, the patient circuit comprising:
    a patient interface;
    a conduit having a first end and an opposite second end, the first end being adapted to be coupled to a pressure generating device; and
    a coupling as recited in claim 3 wherein the first portion is disposed at the second end of the conduit and the second portion is coupled to the patient interface.

* * * * *